United States Patent
Karargyris et al.

(10) Patent No.: US 10,638,926 B2
(45) Date of Patent: May 5, 2020

(54) OPHTHALMOSCOPE USING NATURAL PUPIL DILATION

(71) Applicant: INTERNATIONAL BUSINESS MACHINES CORPORATION, Armonk, NY (US)

(72) Inventors: Alexandros Karargyris, San Jose, CA (US); Thomas G. Zimmerman, Cupertino, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/456,199

(22) Filed: Jun. 28, 2019

(65) Prior Publication Data

US 2019/0313898 A1 Oct. 17, 2019

Related U.S. Application Data

(62) Division of application No. 15/716,596, filed on Sep. 27, 2017, now Pat. No. 10,524,655.

(51) Int. Cl.
| | |
|---|---|
| *A61B 3/12* | (2006.01) |
| *A61B 3/14* | (2006.01) |
| *A61B 3/11* | (2006.01) |
| *A61B 3/00* | (2006.01) |
| *G06K 9/00* | (2006.01) |
| *G06K 9/20* | (2006.01) |

(52) U.S. Cl.
CPC .............. *A61B 3/12* (2013.01); *A61B 3/0091* (2013.01); *A61B 3/112* (2013.01); *A61B 3/14* (2013.01); *G06K 9/0061* (2013.01); *G06K 9/209* (2013.01); *G06K 9/2018* (2013.01); *A61B 3/0025* (2013.01); *G06K 9/00604* (2013.01)

(58) Field of Classification Search
CPC ......... A61B 3/12; A61B 3/0091; A61B 3/112; A61B 3/14
USPC .......................................... 351/205, 206, 246
See application file for complete search history.

(56) References Cited

U.S. PATENT DOCUMENTS

| | | | |
|---|---|---|---|
| 4,238,142 A | 12/1980 | Richards et al. | |
| 5,661,538 A * | 8/1997 | Carter ...................... | A61B 3/11 351/222 |
| 6,089,716 A * | 7/2000 | Lashkari .............. | A61B 3/1241 351/205 |
| 6,276,798 B1 | 8/2001 | Gil et al. | |
| 6,992,775 B2 | 1/2006 | Soliz et al. | |
| 7,854,510 B2 | 12/2010 | Verdooner et al. | |

(Continued)

FOREIGN PATENT DOCUMENTS

| | | |
|---|---|---|
| JP | 0576496 A | 3/1993 |
| WO | 2009129624 A1 | 10/2009 |
| WO | 2019064171 A1 | 4/2019 |

OTHER PUBLICATIONS

IBM: List of IBM Patents or Patent Applications Treated as Related (Appendix P), Jul. 17, 2019, pp. 1-2.

(Continued)

*Primary Examiner* — James R Greece
(74) *Attorney, Agent, or Firm* — Reza Sarbakhsh

(57) ABSTRACT

An ophthalmic device having a single or dual compartment configuration selectively emits infrared and visible light beams onto one or a pair of target eyes. The device performs eye fundus imaging and aids in the detection of ailments as indicated by anomalies in the pupillary reflex.

6 Claims, 13 Drawing Sheets

(56) References Cited

U.S. PATENT DOCUMENTS

| | | | |
|---|---|---|---|
| 8,807,751 B2 | 8/2014 | Kahn et al. | |
| 9,060,718 B2 | 6/2015 | Lawson et al. | |
| 2007/0236663 A1* | 10/2007 | Waldorf | A61B 3/112 351/206 |
| 2009/0174865 A1 | 7/2009 | Privitera et al. | |
| 2009/0225277 A1 | 9/2009 | Gil | |
| 2011/0273669 A1 | 11/2011 | Abitbol et al. | |
| 2012/0092619 A1* | 4/2012 | Rowe | A61B 3/0016 351/221 |
| 2012/0101371 A1 | 4/2012 | Verdooner | |
| 2013/0301004 A1 | 11/2013 | Kahn et al. | |
| 2015/0098059 A1 | 4/2015 | Ou-Yang et al. | |
| 2019/0090739 A1 | 3/2019 | Karargyris et al. | |

OTHER PUBLICATIONS

Pending U.S. Appl. No. 16/456,231, filed Jun. 28, 2019, entitled: Ophthalmoscope Using Natural Pupil Dilation, 69 pages.
Pending U.S. Appl. No. 16/456,246, filed Jun. 28, 2019, entitled: Ophthalmoscope Using Natural Pupil Dilation, 65 pages.
Zimmer et al., "Innovation in Diagnostic Retinal Imaging: Multispectral Imaging", Cover Story, Retinal Today, Oct. 2014, pp. 94-99.
Ellis, "The pupillary light reflex in normal subjects", British Journal of Ophthalmology, 1981 (Best Date Available), 65, pp. 754-759.
Annidis Corporation, http://www.annidis.com/, RHA Report, Clinical Cases,Testimonials of the Month, printed Jun. 5, 2017, pp. 1-3.
Medgaget, "Smartphone App to Help Diagnose Concussions Anywhere and Without Expensive Equiupment," https://www.medgadget.com/2017/09/smartphone-app-help-diagnose-concussions-anywhere-without-expensive-equipment.html, Sep. 7, 2017, pp. 1-6.
Mell et al., "The NIST Definition of Cloud Computing," National Institute of Standards and Technology, U.S Department of Commerce, Special Publication 800-145, Sep. 2011, pp. 1-7.
International Search Report and Written Opinion for International Application No. PCT/IB2018/057392, International filing date: Sep. 25, 2018, dated Jan. 29, 2019, 10 pages.

\* cited by examiner

<

600 emit, by the infrared light source, infrared light in the direction of the opening for a period of time by energizing the infrared light source via the power source. 604

↓ capture, by the image sensor, a reflection of the infrared light. 608

↓ identify, by the image sensor, an image of an eye by analyzing the captured reflection of the infrared eye. 612

↓ measure, by the image sensor, pupil dilation in the eye by analyzing the identified image of the eye. 616

↓ determine, by the processor, that the pupil is dilated by a first amount greater than or equal to a pre-configured dilation measurement. 620

↓ emit, by the visible light source, at least two beams of visible light in sequence, during a period of time for visible light emission, by energizing the visible light source via the power source, the at least two beams of visible light comprising a first beam of visible light having a first energy and a second beam of visible light having a second energy greater than the first energy. 624

FIG. 6A

600 detect, by the image sensor, a response time of pupil constriction in the eye in response to emitting the at least two beams of visible light. 628

generate, by the processor, a delta report comprising data showing a divergence between the measured response time of pupil constriction and an expected response time of pupil constriction. 632

output, by the I/O device, the delta report. 636

FIG. 6B

600 emit, by the infrared light source, at least two beams of infrared light each having a different energy. 640

capture, by the image sensor, a reflection of each of the at least two beams of infrared light. 644

outputting, by the I/O device, one or more images of the captured reflection of each of the at least two beams of infrared light. 648

FIG. 6C

700 emit, by respective infrared light sources of the first compartment and the second compartment, infrared light in the direction of the opening for a period of time by energizing the infrared light source via the power source. 704

capture, by respective image sensors of the first compartment and the second compartment, a reflection of the infrared light. 708

identify, by respective image sensors of the first compartment and the second compartment, an image of an eye by analyzing the captured reflection of the infrared eye. 712

measure, by respective image sensors of the first compartment and the second compartment, pupil dilation in the eye by analyzing the identified image of the eye. 716

determine, by the processor, for each of the first compartment and the second compartment, that the pupil is dilated by a first amount greater than or equal to a pre-configured dilation measurement. 720

emit, by either or both of respective visible light sources of the first compartment and the second compartment, at least two beams of visible light in sequence in one compartment, during a period of time for visible light emission, by energizing the visible light source via the power source, the at least two beams of light comprising a first beam of visible light having a first energy and a second beam of visible light having a second energy greater than the first energy. 724

FIG. 7A

700 detect, by the image sensor, a response time of pupil constriction in the eye in response to emitting the at least two beams of visible light in the first compartment, the second compartment, or both. 728

generate a delta report comprising data showing a divergence between the measured response time of pupil constriction and an expected response time of pupil constriction. 732

output, by the I/O device, the delta report. 736

FIG. 7B

700 detect, by the image sensor of the first compartment, a response time of pupil constriction in the eye positioned at the opening of the first compartment, in response to emitting the at least two beams of visible light in the first compartment, wherein emission of the at least two beams of visible light in sequence is exclusive to the first compartment for the period of time for visible light emission . 740

generate a delta report comprising data showing a divergence between the measured response time of pupil constriction of the eye in the first compartment and the measured response time of pupil constriction of the eye in the second compartment . 744

output, by the I/O device, the delta report. 748

FIG. 7C

700 emit, by respective infrared light sources of the first compartment and the second compartment, at least two beams of infrared light each having a different frequency. 752

capture, by respective image sensors of the first compartment and the second compartment, a reflection of each of the at least two beams of infrared light. 756

output, by the I/O device, one or more images of the captured reflection of each of the at least two beams of infrared light in the first compartment and the second compartment. 760

FIG. 7D

OPHTHALMOSCOPE USING NATURAL PUPIL DILATION

BACKGROUND

Embodiments of the invention generally relate to medical diagnostic devices and procedures, and more particularly to devices and procedures used in ophthalmoscopy.

Medical examination of a patient's eyes typically includes an ophthalmoscopy, a test by which a medical professional, such as an ophthalmologist or a technician, examines and studies the fundus of an eye. During a typical ophthalmoscopy session, the medical professional induces full pupil dilation in the patient's eyes using a chemical agent. Full pupil dilation increases the field-of-view (FOV), i.e. the opening, through which the fundus can be viewed, imaged, and examined. This increased FOV allows the medical professional to examine the eye's internal anatomic structures using visual inspection under white light, and using various devices and imaging techniques that, absent full pupil dilation, is believed, in the prior art, to produce little or no beneficial results.

Chemically-induced pupil dilation is typically performed using eye drops administered by a trained and qualified medical professional. After administering the eye drops, the medical professional and the patient must wait for tens of minutes for full and proper dilation to occur. Thereafter, the pupils remain dilated for many hours.

SUMMARY

Embodiments of the invention generally include ophthalmic devices and methods for their operation and use. In the summary description of embodiments of the invention, references to first, second, and third exemplary apparatuses are made for clarity. It shall be apparent to a person of the ordinary skill that ophthalmic devices may be configured in numerous ways. Therefore, embodiments of the invention should not be construed as limited to the specific arrangements described below in summary form.

A first exemplary apparatus, according to an embodiment of the invention, includes a power source, a light source, and image sensor, a lens, and a housing unit. The light source includes an infrared light source and a visible light source, and the light source is operatively connected to the power source. The image sensor is positioned adjacent to the light source along a first axis, and the light source is either inline or coaxial relative to the image sensor. The lens is positioned between the light source and the image sensor, inline relative to the image sensor along the first axis. The housing unit may include the power source, the light source, the image sensor, or the lens, or any combination thereof, and further includes an opening having an external-light blocking eyepiece. The opening is positioned adjacent to the light source opposite the lens and inline relative to the lens along the first axis.

According to an embodiment of the invention, the first exemplary apparatus further includes a control unit having a processor and a tangible storage device storing program instructions executable by the processor. By executing the program instructions, the ophthalmic device operates as follows. The infrared light source emits infrared light in the direction of the opening for a period of time by energizing the infrared light source via the power source. The image sensor captures a reflection of the infrared light. The image sensor identifies an image of an eye by analyzing the captured reflection of the infrared light. The image sensor measures pupil dilation in the eye by analyzing the identified image of the eye. The processor determines that the pupil is dilated by a first amount greater than or equal to a preconfigured dilation measurement.

According to an embodiment, executing the program instructions causes the first exemplary apparatus to operate as follows. The visible light source emits at least two beams of visible light in sequence, during a period of time for visible light emission, by energizing the visible light source via the power source. The at least two beams of visible light include a first beam of visible light having a first energy and a second beam of visible light having a second energy greater than the first energy.

According to an embodiment, in the first exemplary apparatus, the period of time for visible light emission is greater than zero and less than or equal to 200 milliseconds. According to an embodiment, each of the at least two beams of visible light are emitted for an equal portion of the period of time for visible light emission.

According to an embodiment, the first exemplary apparatus includes an input/output (I/O) device, and executing the program instructions further causes the apparatus to operate as follows. The image sensor detects a response time of pupil constriction in the eye in response to emitting the at least two beams of visible light. The processor generates a delta report that includes data showing a divergence between the measured response time of pupil constriction and an expected response time of pupil constriction. The I/O device outputs the delta report.

According to an embodiment, the first exemplary apparatus includes an input/output (I/O) device, and executing the program instructions further causes the apparatus to operate as follows. The infrared light source emits a beam of infrared light. The image sensor captures a reflection of each of the at least two beams of infrared light. The I/O device outputs one or more images of the captured reflection of each of the at least two beams of infrared light.

According to an embodiment of the invention, in the first exemplary apparatus, the image sensor is coaxial relative to the light source, and the apparatus further comprises. A mirror is positioned inline relative to the image sensor and the lens along the first axis, and inline relative to the light source along a second axis. The first axis is perpendicular relative to the second axis.

According to an embodiment of the invention, a second exemplary apparatus includes a housing unit. The housing unit includes a first compartment and a second compartment operatively connected to one or more power sources. Each of the first compartment and the second compartment include a light source, and image sensor, a lens, and an opening. The light source includes an infrared light source and a visible light source. The light source is operatively connected a power source. The image sensor is positioned adjacent to the light source along a first axis. The light source is either inline or coaxial relative to the image sensor. The lens is positioned between the light source and the image sensor, inline relative to the image sensor along the first axis. The opening has an external-light blocking eyepiece. The opening is positioned adjacent to the light source opposite the lens and inline relative to the lens along the first axis.

According to an embodiment of the invention, the second exemplary apparatus includes at least one control unit having a processor and a tangible storage device storing program instructions executable by the processor. When executed, the program instructions cause the second exemplary apparatus to operate as follows. Respective infrared light sources of the first compartment and the second compartment emit infrared light in the direction of the opening for a period of time by energizing the infrared light source via the power source. Respective image sensors of the first compartment and the second compartment capture a reflection of the infrared light. Respective image sensors of the first compartment and the second compartment identify an image of an eye by analyzing the captured reflection of the infrared light. Respective image sensors of the first compartment and the second compartment measure pupil dilation in the eye by analyzing the identified image of the eye. The processor determines, for each of the first compartment and the second compartment, that the pupil is dilated by a first amount greater than or equal to a pre-configured dilation measurement.

According to an embodiment of the invention, executing the program instructions of second exemplary apparatus cause the second exemplary apparatus to operate as follows. Either or both of respective visible light sources of the first compartment and the second compartment emit at least two beams of visible light in sequence in one compartment, during a period of time for visible light emission, by energizing the visible light source via the power source. The at least two beams of light include a first beam of visible light having a first energy and a second beam of visible light having a second energy greater than the first energy.

According to an embodiment of the invention, in the second exemplary apparatus, the period of time for visible light emission is greater than zero and less than or equal to 200 milliseconds. According to an embodiment of the invention, each of the at least two beams of visible light are emitted for an equal portion of the period of time for visible light emission.

According to an embodiment of the invention, the second exemplary apparatus further includes an input/output (I/O) device. Executing the program instructions of second exemplary apparatus cause the second exemplary apparatus to operate as follows. The image sensor detects a response time of pupil constriction in the eye in response to emitting the at least two beams of visible light in the first compartment, the second compartment, or both. A delta report is generated. The delta report includes data showing a divergence between the measured response time of pupil constriction and an expected response time of pupil constriction. The I/O device outputs the delta report.

According to an embodiment of the invention, the second exemplary apparatus further includes an input/output (I/O) device, and executing the program instructions causes the second exemplary apparatus to operate as follows. The image sensor of the first compartment detects a response time of pupil constriction in the eye positioned at the opening of the first compartment, in response to emitting the at least two beams of visible light in the first compartment. Emission of the at least two beams of visible light in sequence is exclusive to the first compartment for the period of time for visible light emission. A delta report is generated. The delta report includes data showing a divergence between the measured response time of pupil constriction of the eye in the first compartment and the measured response time of pupil constriction of the eye in the second compartment. The I/O device outputs the delta report.

According to an embodiment of the invention, in the second exemplary apparatus, the control unit further includes an input/output (I/O) device, and executing the instructions of the second exemplary apparatus cause the second exemplary apparatus cause the second exemplary apparatus to operate as follows. Respective infrared light sources of the first compartment and the second compartment emit a beam of infrared light. Respective image sensors of the first compartment and the second compartment capture a reflection of each of the at least two beams of infrared light. The I/O device outputs one or more images of the captured reflection of each of the at least two beams of infrared light in the first compartment and the second compartment.

According to an embodiment of the invention, a third exemplary apparatus includes a pair of light emitting devices, one or a pair of openings, a pair of image sensors, and a pair of lenses. The pair of light emitting devices is configured to emit light onto a pair of target eyes. The light includes infrared light and visible light. The one or pair of openings is configured to couple with the pair of target eyes to block light external to the apparatus from hitting the pair of target eyes. The pair of image sensors is configured to capture light reflected from the pair of target eyes. The pair of lenses is configured to focus light reflected from the pair of target eyes onto the pair of image sensors.

According to an embodiment of the invention, the third exemplary apparatus further includes a controller unit configured to illuminate the pair of target eyes with a plurality of successively more energetic light beams within a period of time.

According to an embodiment of the invention, an exemplary method for examining a pair of target eyes of a patient using an exemplary apparatus performs the following steps. The method covers the pair of target eyes with a pair of external-light blocking eyepieces of the apparatus. The covering includes positioning the pair of external-light blocking eyepieces in contact with the patient's face. The method includes monitoring pupil dilation of the target pairs of eyes for a period of time while the pair of external-light blocking eyepieces are in contact with the patient's face, and further includes emitting, by a pair of light sources of the apparatus based on the monitoring, infrared light at the pair of target eyes. The method also includes detecting, using a pair of image sensors of the apparatus, infrared light reflected by the pair of target eyes in response to the emission of infrared light by the pair of light sources.

According to an embodiment of the invention, in the exemplary method, the step of monitoring includes detecting pupils of the target pairs of eyes reaching maximum dilation.

According to an embodiment of the invention, the exemplary method further includes the step of emitting, selectively by one of the light sources towards a first eye in the pair of target eyes, at least two beams of visible light in sequence, during a period of time for visible light emission, by energizing the light source via a power source. The at least two beams of light include a first beam of visible light having a first energy and a second beam of visible light having a second energy greater than the first energy.

According to an embodiment of the invention, the exemplary method also includes capturing images of the first eye and the second eye. The method further includes measuring, based on the captured images, a response time of pupil constriction in the first eye relative to pupil constriction in a second eye in the pair of target eyes. The method also includes generating a delta report comprising data showing a divergence between the measured response times of pupil constriction in the first eye and the second eye. The method also includes outputting, by an I/O device of the apparatus, the delta report.

According to an embodiment of the invention, in the exemplary method, the period of time for visible light emission is greater than zero and less than or equal to 200 milliseconds.

According to an embodiment of the invention, in the exemplary method, the emitting further includes emitting, selectively by one of the light sources towards a first eye in the pair of target eyes, at least one beam for each distinct visible light spectrum color, in sequence from least energized to most energized.

According to an embodiment of the invention, in the exemplary method, pupil dilation during at least a portion of the period of time for visible light emission is less than 100%.

BRIEF DESCRIPTION OF THE SEVERAL VIEWS OF THE DRAWINGS

FIG. 6A is a flowchart of a method for using the ophthalmic device of FIGS. 1-3, according to an embodiment of the invention.

FIG. 6B is a flowchart of a method for using the ophthalmic device of FIGS. 1-3, according to an embodiment of the invention.

FIG. 6C is a flowchart of a method for using the ophthalmic device of FIGS. 1-3, according to an embodiment of the invention.

FIG. 7A is a flowchart of a method for using the ophthalmic device of FIGS. 1 and 4-5, according to an embodiment of the invention.

FIG. 7B is a flowchart of a method for using the ophthalmic device of FIGS. 1 and 4-5, according to an embodiment of the invention.

FIG. 7C is a flowchart of a method for using the ophthalmic device of FIGS. 1 and 4-5, according to an embodiment of the invention.

FIG. 7D is a flowchart of a method for using the ophthalmic device of FIGS. 1 and 4-5, according to an embodiment of the invention.

DETAILED DESCRIPTION

Figure 1:
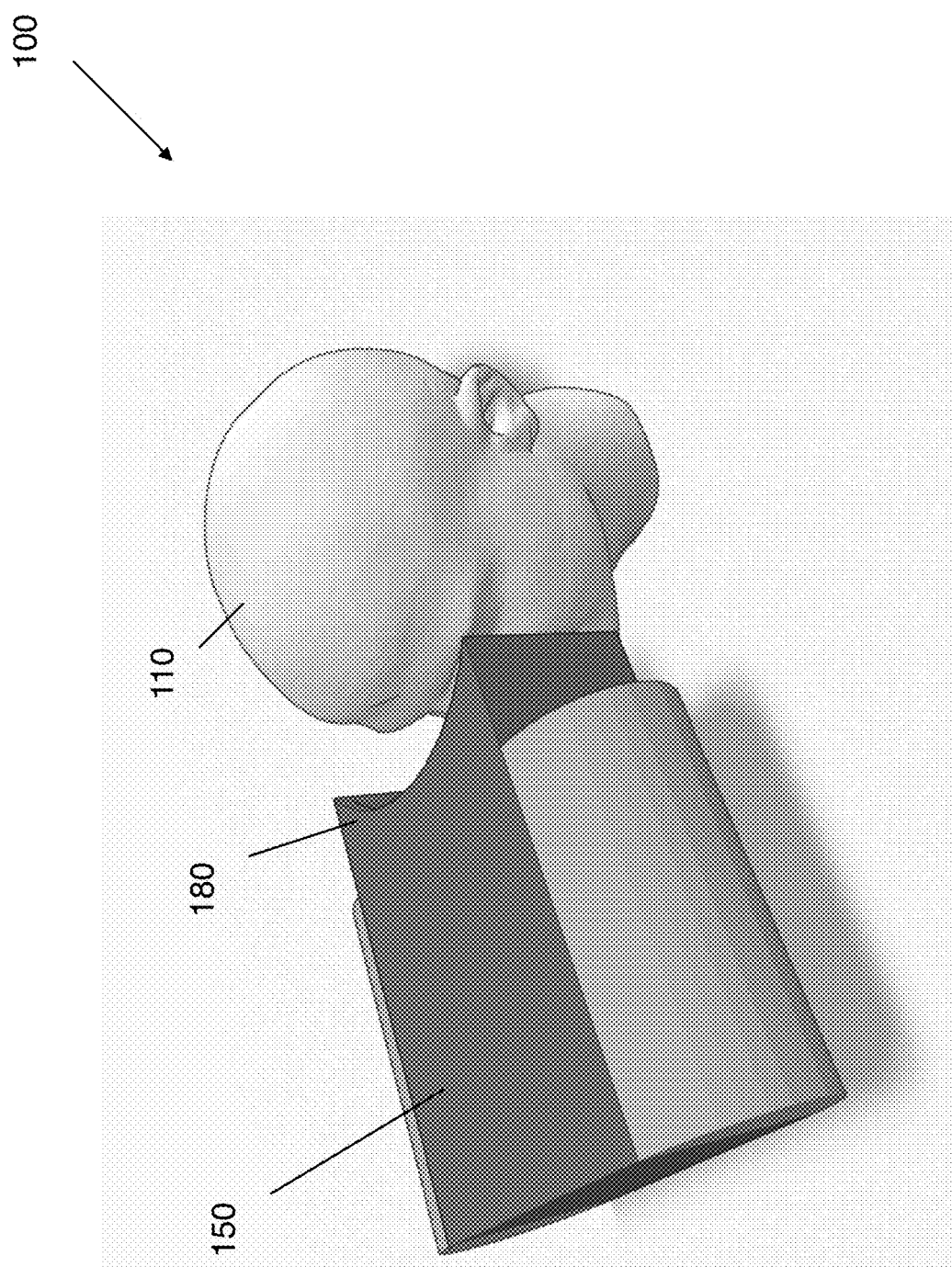
FIG. 1 is a diagram of a medical diagnostic environment 100 including a user 110 and an ophthalmic device 150, according to an embodiment of the invention.

There are several significant medical and practical disadvantages to current ophthalmoscopy equipment and procedures. It is taken as a fact of life that patients and medical professionals must endure the disadvantages of these practices, and it is accepted that millions of people around the world simply cannot have access to regular treatment. This is particularly the case since there is no known alternative except to forgo the examination altogether or to perform other examinations that have limited benefits and incomplete results.

Embodiments of the invention address at least four categories of problems in this area: (1) pupil dilation inducement, (2) in-turn examination, (3) synchronicity, and (4) mobility and scale.

Pupil Dilation Inducement.

Chemically-induced pupil dilation causes patients discomfort for an extended period of time. The patient's eyes remain dilated far longer than necessary to perform the ophthalmoscopy. While the patient's pupils are dilated, the patient can experience blurred vision, transient stinging, increased intraocular pressure, redness, inflammation, and sensitivity to light. The patient must wear uncomfortable dark glasses to protect the patient's eyes, even from natural light.

Practically, chemically-induced pupil dilation inconveniences both the patient and the medical professional. The procedure limits the patient's post-examination activities (for example, the patient cannot drive or read). Therefore, the patient may have to take a day off from work, or make an appointment later in the day (which limits schedule flexibility). The medical professional and her medical practice may be inconvenienced since they may otherwise wish to spread appointments throughout the day, instead of in the afternoon. Additionally, only select medical professionals can administer mydriatics (dilation-inducing eye drops). This limits the geographic coverage area to places where a trained medical professional is physically present and available to administer the mydriatics. Furthermore, since the patient's pupils take tens of minutes to fully dilate, the medical professional must administer the chemical agent far sooner than the examination can begin. This extends appointment times for both the medical professional and the patient, and limits the amount of care the medical professional can provide and the number patients she can examine. While the pupils are dilating, the patient is not receiving care and the medical professional is not providing care; they are simply waiting. During examination, the examination room must remain dark to accommodate the patients' hypersensitivity to visible light. Working in a dark room poses obvious difficulties for work and movement, for both the patient and the medical professional.

Furthermore, current examination procedures and devices require full pupil dilation, and perform no quantitative diagnostic analysis of eye behavior in the constriction phase where pupil dilation is less than 100%. This is because the primary objective of these procedures and devices is to examine the eye's fundus. Full pupil dilation is thought to be ideal during fundus examination because it provides the greatest FOV for examination. For any given size of an image of the fundus captured by an imaging device, the area of interest in the image will likely be higher the more dilated the pupils are.

In-Turn Examination.

Existing ophthalmoscopy procedures, including multispectral imaging processes, measure eye behavior and pupil dilation and constriction for each eye, in turn. For example, existing multispectral imaging tools are used to examine only one eye at a time. Simultaneous examination of both eyes of a patient is not performed because its benefits are not recognized or appreciated in the prior art. Rather, in the prior art, configuring the device to perform simultaneous examination is seen as a drawback, because it will require doubling the examination infrastructure. The cost alone is reason enough, in the prior art, not to perform simultaneous examination of both eyes using such devices, because the prior art does not recognize any benefits.

Synchronicity.

Existing ophthalmic examination devices do not apply beams of visible light to a patient's eyes asymmetrically or asynchronously.

Asynchronous pupil constriction in a first eye in response to visible light stimulation of a second eye can be indicative of various eye ailments in the first eye, the second eye, in both eyes, or in other parts of the optic system that are involved in the synchronous pupil dilation and constriction response. When the first eye having a dilated pupil is stimulated with a visible light beam, it constricts. In a healthy patient, constriction of the first eye in response to stimulus results in synchronous pupil constriction in the second eye, even if the second eye is not directly stimulated. Highly pronounced instances of asynchronous pupil constriction may be qualitatively detected by a visual examination technique, but require a trained expert medical professional, often an ophthalmologist herself, to make the detection. However, a subtle yet significant lack of synchronicity is impossible to detect using visual examination. This limitation significantly affects patient care because it makes early detection impossible. When the diagnosis is finally made through manual examination, there are more severe symptoms, greater complications, and fewer available treatments options. Any available treatment option is likely to be less effective than if the ailment was diagnosed sooner.

Furthermore, manual observation of asynchronous pupil constriction, even by a trained expert medical professional, is a qualitative assessment. Humans lack the perceptual ability to quantify (e.g., in milliseconds), temporal asynchronous pupil constriction.

Mobility and Scale.

Although great advancements are made regularly in ophthalmology, an unfortunate consequence of the three previously outlined limitations of the prior art in ophthalmic examination techniques and devices is that these techniques and devices cannot be easily practiced and used outside of an immobile medical establishment. With respect to the examination techniques at issue, providing such examination requires a patient to travel to an ophthalmologist's office. Logistic considerations mean that patients, even those with considerable material resources, must often wait for months for an appointment with a reputable practitioner. For most of the planet's population, regular visits to an ophthalmologist is a luxury. Clearly, the current model of ophthalmic care is not mobile, and is not scalable.

Accordingly, there is a significant unrecognized and unmet need to overcome these and other limitations of the prior art. Some embodiments of the invention may provide solutions to one or more of these needs.

Generally, embodiments of the invention provide for ophthalmic examination devices, and methods for their operation and use. Some of these ophthalmic devices may induce pupil dilation naturally, and examine both eyes simultaneously but asynchronously when needed. It shall be understood by a person of ordinary skill in the art that embodiments of the invention need not have elements that serve each one of these considerations, nor is it necessary for embodiments of the invention to satisfy any of these considerations to meet the threshold for novelty and non-obviousness. The invention is defined by the claims.

An exemplary embodiment of the invention provides for a wearable device, such as a goggle or mask, or a mounted device, such as a floor mounted, table mounted, or mobile examination device, that interfaces with a patient's face by covering one or both of the patient's eyes, and optionally the surrounding facial structure, to induce natural pupil dilation. Using a combination of infrared and visible light sources, and further using various configurations and methods of emitting light beams by these light sources, embodiments of the invention use image sensors to capture the condition of the patient's eyes and their responses to stimuli, to detect anomalies and to diagnose ailments.

In the exemplary embodiment, the ophthalmic device is configured to communicate with a cloud-based software service for providing medical diagnostics and medical recommendations, particularly in geographic environments where traditional ophthalmic facilities, devices, and procedures are limited.

In the embodiment where the device is a wearable device (e.g., a goggle or portable mask), the device can be provided at homes or remote locations, and even outdoors, where ophthalmic care is difficult to provide or not readily available. Patient care and coverage area are immensely improved.

Embodiments of the invention will now be discussed in connection with the Figures. The Figures illustrate exemplary, non-limiting, and alternative embodiments of the invention. Before discussing each figure in detail, a general overview of some of the figures is provided. The general overview will be instructive to a person of ordinary skill in the art to recognize the problems that exist in the prior art, identify and practice the specific solutions that embodiments of the invention provide, and recognize the results that can be achieved.

As an overview; FIG. 1 illustrates a general examination environment including a user (also referred to as a patient) and one exemplary ophthalmic device. FIG. 1 illustrates how the ophthalmic device can be shaped (via one or more openings) to interface with the patient to cover the patient's eyes and to block external light beams (i.e., light beams emitted from a source other than the ophthalmic device) from radiating onto the patient's eye. This mechanism isolates the eyes and induces natural pupil dilation without the need for mydriatics. The ophthalmic device shown in FIG. 1 can have at least one or at least two compartments. In the dual-compartment configuration, each compartment accommodates an eye to be examined.

Figure 2:
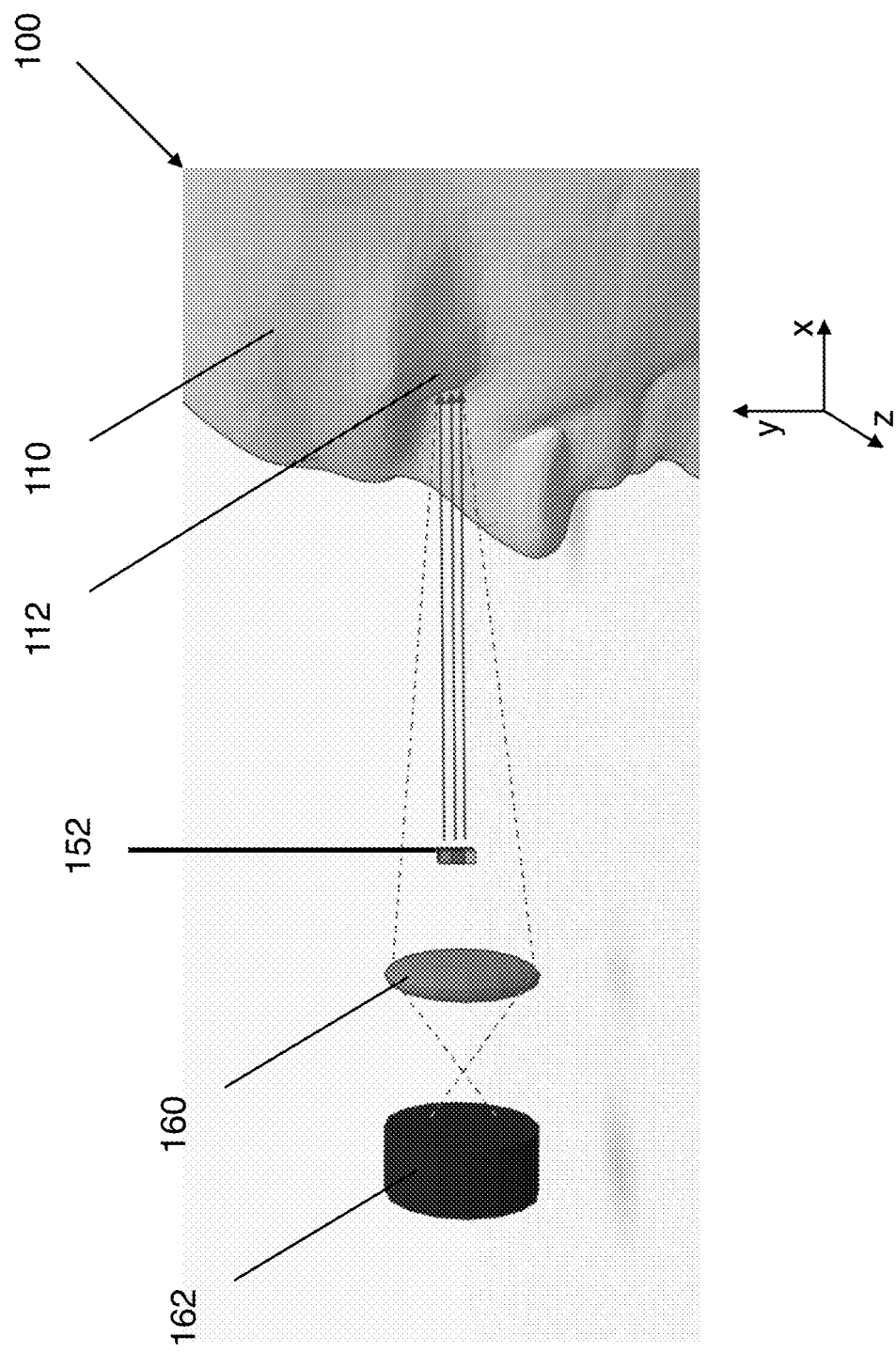
FIG. 2 is a partial diagram of the medical diagnostic environment 100 of FIG. 1, including select components of at least one compartment of ophthalmic device 150, arranged inline, according to an embodiment of the invention.
Figure 3:
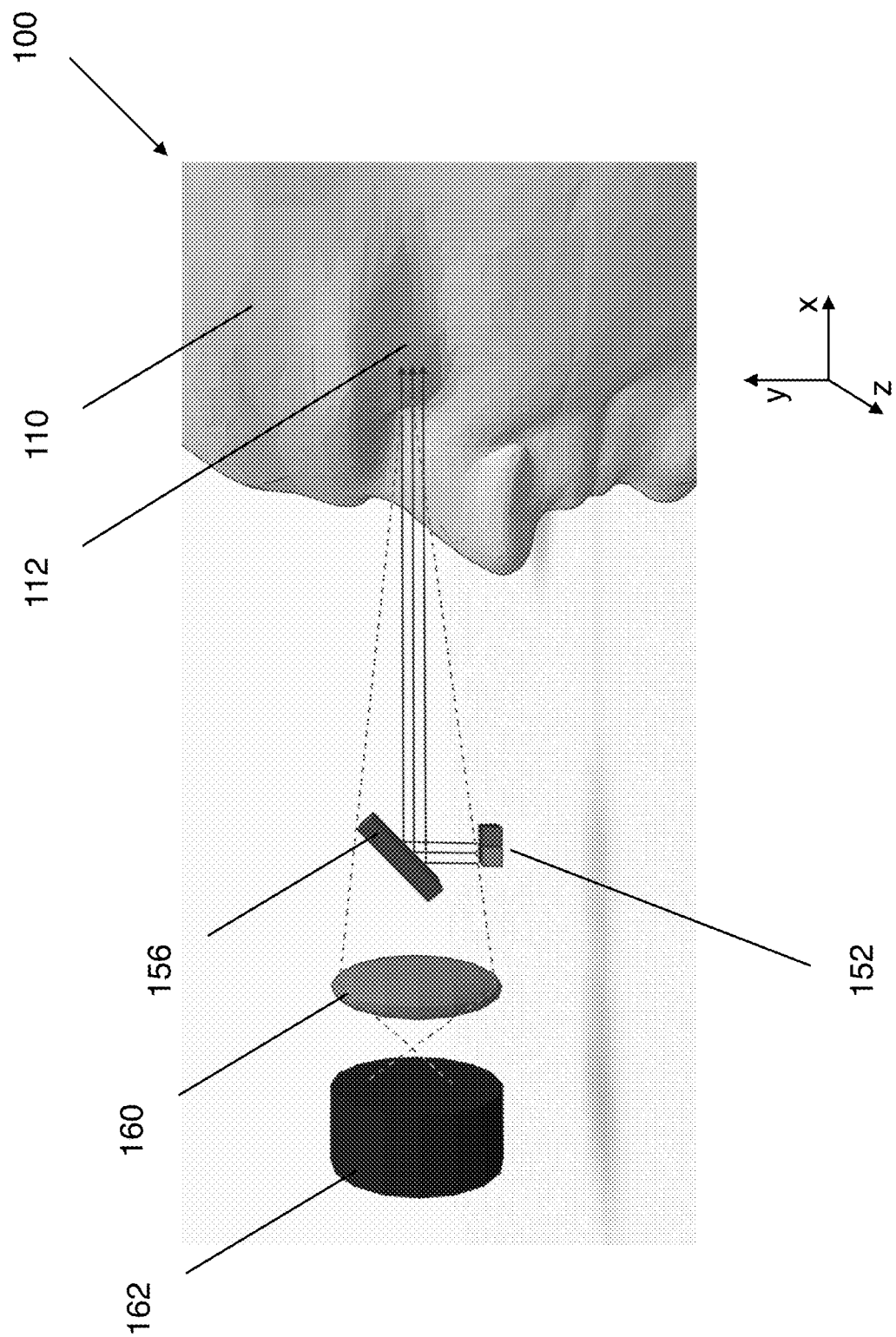
FIG. 3 is a partial diagram of the medical diagnostic environment 100 of FIG. 1, including select components of at least one compartment of ophthalmic device 150, arranged coaxially, according to an embodiment of the invention.

FIGS. 2 and 3 illustrate exemplary configurations of the various internal components of a single compartment of the ophthalmic device of FIG. 1. That is, any given compartment of the ophthalmic device may include any configuration as provided in FIGS. 2 and 3.

Figure 4:
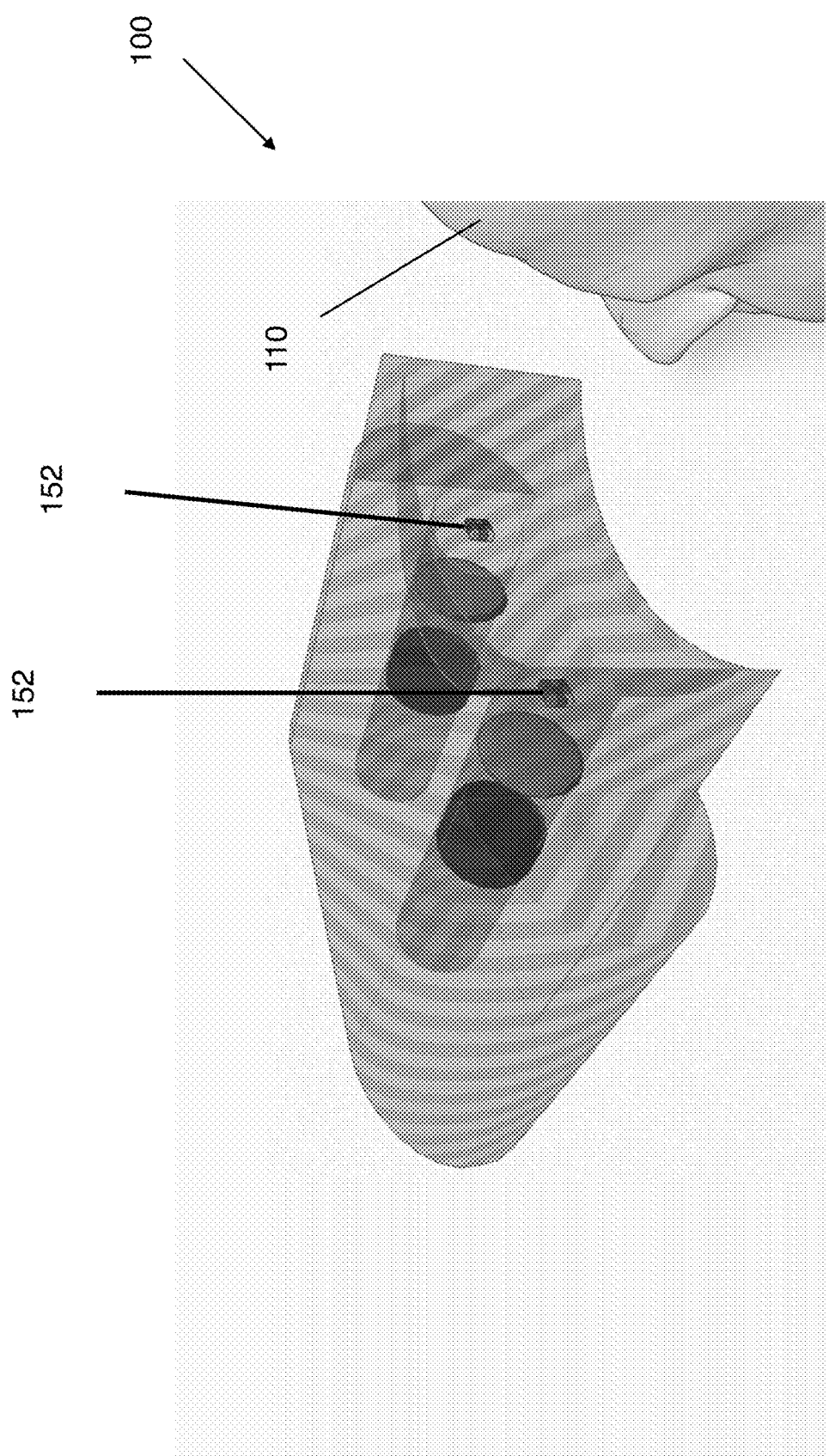
FIG. 4 is a partial diagram of a dual-compartment configuration of the medical diagnostic environment 100 of FIGS. 1 and 2, including select components of ophthalmic device 150, arranged inline, according to an embodiment of the invention.
Figure 5:
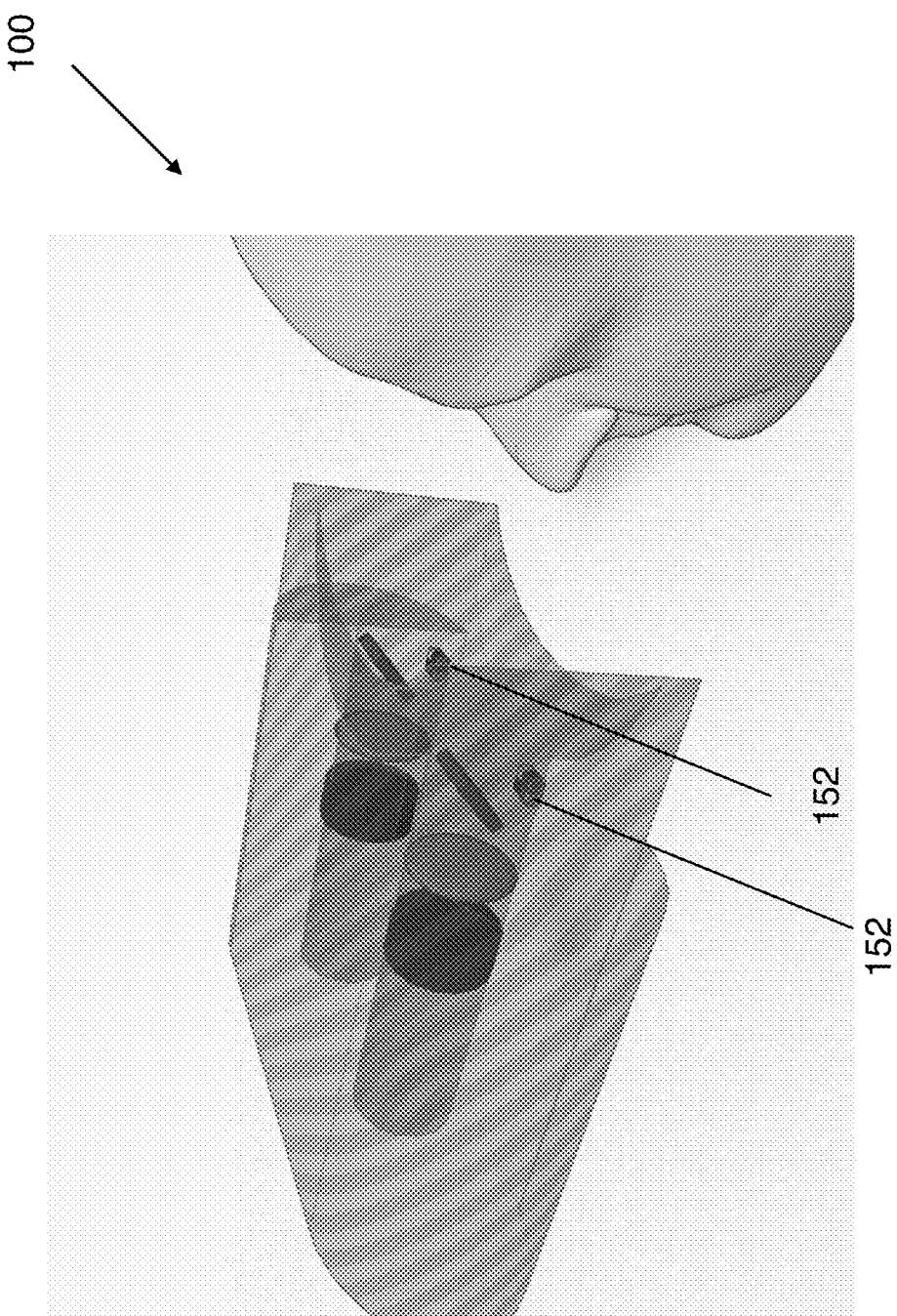
FIG. 5 is a partial diagram of a dual-compartment configuration of the medical diagnostic environment 100 of FIGS. 1 and 3, including select components of ophthalmic device 150, arranged coaxially, according to an embodiment of the invention.

FIGS. 4 and 5 illustrate exemplary dual-compartment configurations of the ophthalmic device of FIG. 1. Each compartment of the dual-compartment configuration of FIGS. 4 and 5 may be a single compartment as provided in FIGS. 2 and 3. It is possible to mix and match these configurations in the dual-compartment configuration.

FIGS. 6A-C and 7A-D are flowcharts of exemplary methods of using the ophthalmic device of FIG. 1.

Figure 8:
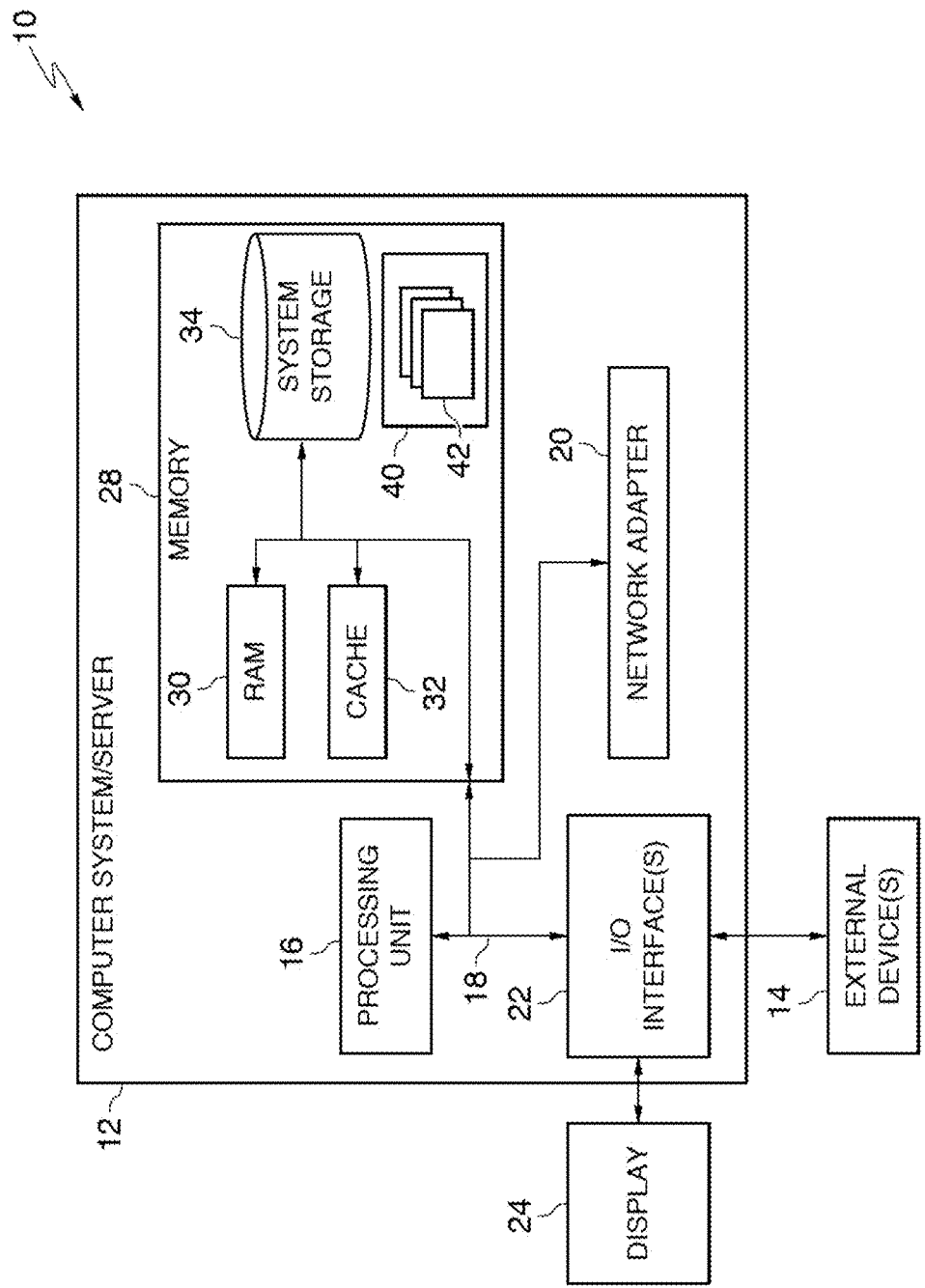
FIG. 8 is a block diagram of a cloud computing node (computing device) that may be incorporated into or operatively connected to the ophthalmic device of FIGS. 1-5 to perform the methods of FIGS. 6A-C and 7A-D, according to an embodiment of the invention.

FIG. 8 depicts an exemplary cloud computing node (computing device) that performs and coordinates various computing functions and operations of the ophthalmic device of FIG. 1. The computing device of FIG. 8 can be a control chip (or any other suitable device) operatively coupled with the ophthalmic device. For example, it may be a computing chip housed within or operatively connected to any compartment of the ophthalmic device. The computing device could alternatively be integrated into particular components of ophthalmic device. For example, the computing device (including, for example, its processor) may be the same as, or a part of, one or more image sensors of the ophthalmic device.

Figure 9:
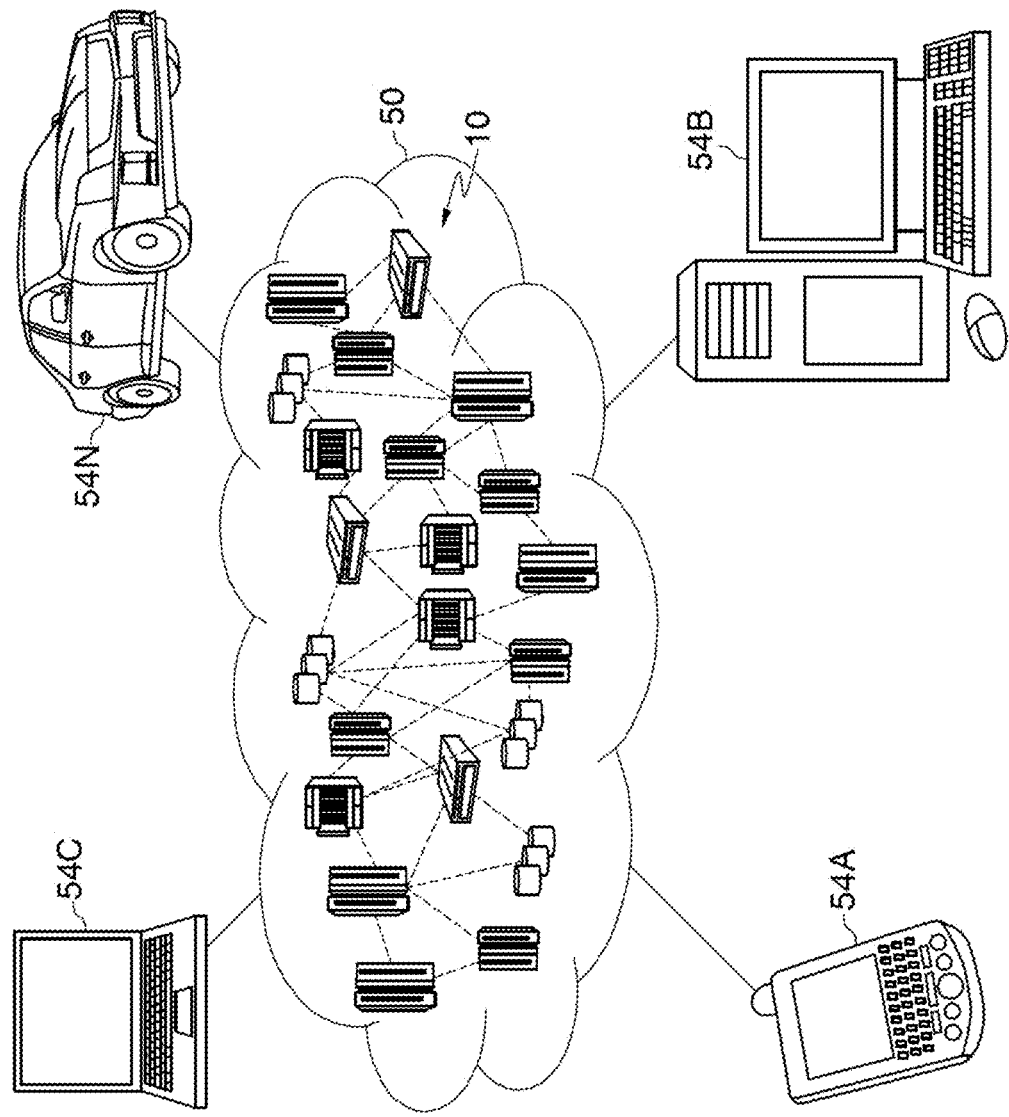
FIG. 9 is a block diagram of a cloud computing environment including the cloud computing node of FIG. 8, according to an embodiment of the invention.
Figure 10:
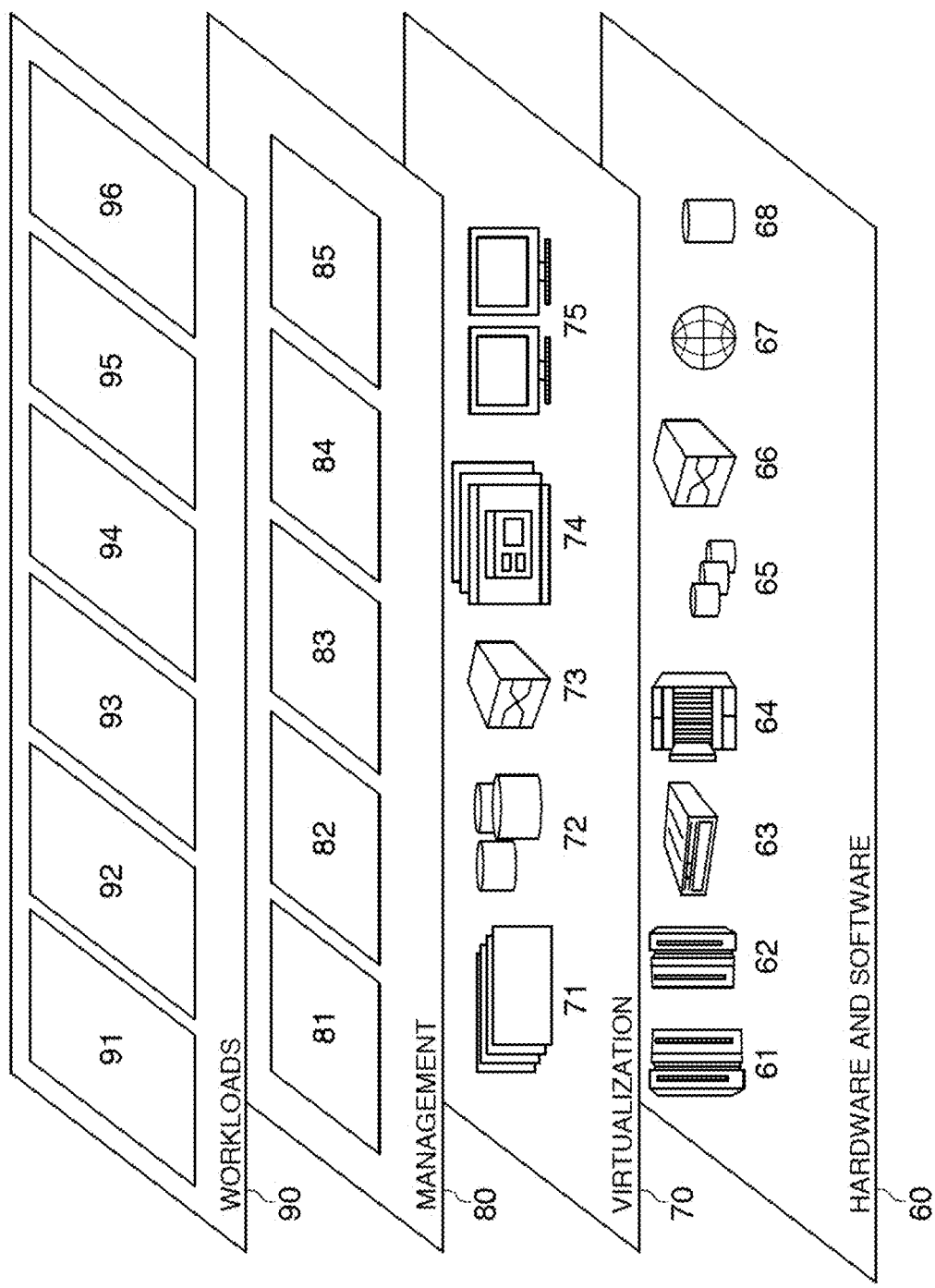
FIG. 10 is a block diagram of functional layers of the cloud computing environment of FIG. 9, according to an embodiment of the invention.

FIGS. 9 and 10 depict aspects of a cloud computing environment and its functional layers, respectively, for providing medical diagnostic and analysis services. The ophthalmic device of FIG. 1 may connect to the cloud environment to communicate images that it captures, to enable the cloud service to perform imaging analysis, medical diagnostic analysis, or any other form of analysis that is required. Alternatively, some or all of these functions can be performed locally on the ophthalmic device, and the results can be communicated to the cloud service.

Having recited a broad overview of the figures, embodiments of the invention will now be described in greater detail with direct reference to the figures.

FIG. 1 is a diagram of a medical diagnostic environment 100 including a user 110 (also referred to as "patient") and an ophthalmic device 150, according to an embodiment of the invention. Medical diagnostic environment 100 may be, for example, an outdoor space, or an indoor space such as a room in a hospital or a medical office building, or any other geographic area where user 110 is present. It shall be clear to a person of ordinary skill in the art that features of at least some embodiments of the invention allow deployment of ophthalmic device 150 to makeshift medical theaters or even a patient's home.

With continued reference to FIG. 1, according to an embodiment of the invention, ophthalmic device 150 may be a wearable goggle, a floor or table mounted apparatus, or otherwise configured to be placed in contact with the patient's face in order to allow for imaging of the patient's eyes. Ophthalmic device 150 includes one or more compartments, and a patient-facing side 180 having one or more openings. The patient-facing side 180 of ophthalmic device 150 is equipped with one or more external-light blocking components. In an embodiment, the external-light blocking component may include a padded or rubber strip that is contoured, i.e. affixed to, the rim of patient-facing side 180. Either or both of patient-facing side 180 and the external-light blocking components may be curved, or otherwise shaped to receive a patient's face. For example, patient-facing side 180 or the external-light blocking components may be contoured using a face-molding process, such that when the patient's face is placed at patient-facing side 180, the external light blocking components block all or substantially all light from reaching the patient's eyes. In an embodiment, patient-facing side 180 may include two openings, where an eyepiece is attached to each of the two openings. The two eyepieces may be similar to goggles or eyepieces used in microscopes, point-and-shoot cameras, ski mask googles, and virtual reality goggles. Such eyepieces may be shaped to match the eye socket or an area of a user's head. Any known configuration in the art may be used to achieve the desired effect, i.e., to completely or substantially block external light from hitting the user's eyes. The phrase "substantially block" means blocking external light beams from radiating onto the patient's eye(s) to prevent pupil constriction by more than a threshold factor. The threshold factor may be user-defined, preconfigured, and adjustable (e.g., by a technician or an ophthalmologist).

In embodiments where ophthalmic device 150 is a mobile wearable device, a fastening apparatus (such as an elastic or adjustable plastic strap) may be attached to opening 180 or another portion of ophthalmic device 150 to secure the apparatus to the patient's head. This configuration may be particularly ideal for embodiments of the invention where ophthalmic device 150 has a low profile and is light weight. This configuration can be easily and cheaply deployed to makeshift theaters or outdoor spaces.

Blocking a patient's eyes allows the pupils to dilate naturally. This natural pupil dilation inducement process obviates the need for administering mydriatics, and therefore, avoids their negative side effects and drawbacks. For example, maximum natural dilation can be induced in only a few minutes using ophthalmic device 150, without darkening the surrounding area. This enables using ophthalmic device in lit rooms or outdoor spaces. Moreover, natural pupil dilation inducement can be performed by the patient herself or by anyone else, and the patient need not rely on a medical professional or travel to a medical facility. Using ophthalmic device 150, health service providers or medical professionals can provide remote or automatic diagnostic services to patients, particularly those living in remote or impoverished areas with little or no direct access to healthcare facilities or healthcare professionals.

Ophthalmic device 150 may be operatively connected to a control unit (not shown) having a processor and other components described in connection with FIG. 8. Ophthalmic device 150 may house the control unit. The control unit, or the ophthalmic device, may also include one or more input/output (I/O) devices for communicating with one or more users (including the patient or medical professional) and other systems. For example, the I/O devices may include a digital display, a wireless transmitter and receiver (for example, a Bluetooth component), an electric cable, a data recording device, a storage device (such as an SD memory card) or any other I/O device known in the art. In one embodiment, ophthalmic device 150 may communicate to a healthcare cloud environment for providing medical software analysis services. These embodiments are discussed in greater detail in connection with FIGS. 8-10.

Users including a patient or a medical professional can operate ophthalmic device 150 using any mechanism known in the art, including without limitation, a control panel operatively connected to ophthalmic device 150 (e.g., mounted on a surface of the apparatus), or a software application (e.g., mobile app). Additionally, ophthalmic device 150 may be controlled remotely through a cloud based service. The controls may be engaged to start, pause, stop, repeat, or otherwise control the device's functions.

According to an embodiment of the invention, ophthalmic device 150 has the dimensions 125 mm (W)×200 mm (L)×110 mm (H), where the patient-facing side measures 200 mm (although the eyepiece or the actual eye/eye socket fitting may be smaller or larger). Various surfaces may be curved or otherwise shaped to accommodate technical and aesthetic considerations. These dimensions are exemplary.

FIG. 2 is a partial diagram of the medical diagnostic environment 100 of FIG. 1, including select components of at least one compartment of ophthalmic device 150, arranged inline, according to an embodiment of the invention.

The at least one compartment of ophthalmic device 150 may be a component of a larger housing unit. To better illustrate embodiments of the invention, the housing unit and the at least one compartment are not explicitly shown in FIG. 2. The at least one compartment contains a power source, a light source 152, an image sensor 162, and a lens 160. This configuration is for illustrative purposes, and other configurations are possible. For example, the power source need not be housed within the at least one compartment, or within the housing unit. Additionally, while various components are described as being inside the at least one compartment, a person of ordinary skill in the art will understand that these components may be positioned differently to achieve the same results.

The power source may be any energy source known in the art, such as a set of batteries or an electric cord pluggable into an electric outlet, or any other power source generating sufficient power to operate light source 152 and image sensor 162. The term power source is used to generally refer to any component in ophthalmic device 150 that generates power and is operatively connected to power consuming components. The power source or another component of the device may be controlled via a control unit to energize light source 152 or one or more of the individual lights in light source 152.

Light source 152 may be a collection of one or more light emitting devices that generate infrared light, visible light, or both. For example, light source 152 may include one or more visible light sources and one or more infrared light sources. Each of these light sources may be a light emitting diode (LED) light source. For example, the visible light LEDs may each be 1.6×1.6 mm RGB LEDs. The LEDs may be arranged in one or more arrays mounted on a substrate. The LEDs may be positioned in such a way that the substrate blocks light beams from travelling in an unwanted direction. For example, in one inline configuration, the LEDs may be positioned such that the substrate faces the side of the device housing image sensor 160, so as not to directly emit light beams into that image sensor. Otherwise, these light beams may interfere with light beams reflected from the patient's eye. LEDs may be provided as needed to enable emission of infrared light and visible light at various wavelengths, frequencies, or photon energy.

Light source 152, according to embodiments of the invention, can emit both infrared light beams and visible light beams during different time periods, overlapping time periods, or the same time period. In some embodiments where light source 152 emits visible light beams, light source 152 emits at least two visible light beams in increasing energy intensity. Energy intensity may be a function of the visible light beams' wavelength, frequency, or photon energy. For example, a green LED may emit a light beam having a wavelength of ~495-570 nm, an energy of ~526-6-6 THz, and a photon energy of 2.17-2.50 eV. The property of increasing (or ascending) energy intensity is equivalent to the process of increasing photon energy and equivalent to the process of decreasing (descending or shortening) wavelength. The property of decreasing (or descending) energy intensity is equivalent to the process of decreasing photon energy and equivalent to the process of increasing (ascending or elongating) wavelength.

Unlike in the prior art, the choices of light source 152, and their structure and arrangement, as described above, enable several novel processes, including: maximizing the FOV of the fundus during visible light beam emissions (resulting in greater coverage of the captured images of the fundus); simultaneously performing visible light and infrared light imaging. The latter benefit not only saves time, but also allows for simultaneous examination of the pupillary reflex to diagnose ailments where observations of the pupillary reflex are indicators.

Enablement of these novel processes is based at least on the following. Sequential emission of visible light beams with increasing energy intensities results in a controlled and sequential constriction of the pupil. The amount of pupillary constriction usually depends on the energy intensity of the visible light beam radiation; the higher the light beam's energy, the greater and more pronounced the pupil's constriction response. It is an objective of some ophthalmoscopy procedures to capture images of the fundus at various wavelengths of visible and infrared light at maximum possible FOV (via the pupil opening). However, since visible light causes pupil constriction, known procedures yield poor images (i.e., less than maximum possible coverage of the internal structures of the fundus). For example, if the eye is illuminated using green light in the first instance, the pupil responds with maximum constriction and thereby reduces the POV available for fundus imaging using infrared light. Additionally, since constriction moves to its maximum extreme, it becomes impossible to measure subtle variances with expected constriction behavior in the spectrum between minimum and maximum constriction (or between maximum and minimum dilation).

According to some embodiments of the invention, therefore, emission of visible light beams and emissions of infrared light beams by light source 152 can occur simultaneously. That is, as the infrared light beams radiate onto the eye (and as reflections of the infrared light beam are captured by image sensor 162), so do visible light beams. Therefore, ophthalmic device 150 can simultaneously capture fundus structures and measure pupillary reflexes. Additionally, because visible light emissions are sequential and increasing in energy intensity, at any given moment during image capture using infrared light, the impact of visible light on the pupillary reflex is minimized. For example, if a high energy visible light beam was used instead (and not sequentially), the pupil would constrict at an unnecessarily high amount and thereby reduce the opening at which internal structures and surfaces of the fundus could be imaged using infrared light.

With continued reference to FIG. 2, light source 152 is operatively connected to the power source to selectively energize one or more individual LEDs as needed. In the depicted embodiment, light source 152 is positioned inline relative to the user-facing side of the apparatus and relative to other components described below, along a first axis running horizontally across the x-axis relative to the apparatus. Alternatively, light source 152 may be positioned coaxially relative to image sensor 162 (this alternative configuration is shown in FIG. 3). In an embodiment, light source 152 generally may emit an infrared light beam having a wavelength of approximately 900 nm, and a series of visible light beams having wavelengths of approximately 548 nm, 586 nm, 610 nm, and 660 nm.

Image sensor 162 may be any image source known in the art capable of capturing reflections of light including visible light and infrared light, among others. In an embodiment, it is an electronic monochromatic CMOS sensor having an imaging area 3.9×2.5 mm, and can capture 1280×800 resolution images at 120 frames per second. Image sensor 162 may be positioned adjacent to light source 152 along the first axis, i.e. the x-axis. Light source 152 may be positioned inline (FIG. 2) or coaxially (FIG. 3) relative to image sensor 162.

Lens 160 is positioned between light source 152 and image sensor 160, inline relative to image sensor 160 along the first axis, i.e. the x-axis. Lens 160 may be, in an embodiment, a 3.5 mm focal length, eight-element lens with antireflection coating. As light source 152 emits light beams (visible or infrared), the light beams reflect inside the apparatus and illuminate the patient's eyes. As the reflected light beams travel through lens 160, they are focused into image sensor 160, allowing the latter to capture an image of the user's eyes illuminated under visible light or infrared light.

The first compartment includes a housing unit (not shown) that can encompass one or more of the components listed above, i.e., a power source, a light source, an image sensor, a lens, or any combination of them, and further includes an opening having an external-light blocking eyepiece, the opening being positioned adjacent to the light source opposite the lens and inline relative to the lens along the first axis.

FIG. 3 is a partial diagram of the medical diagnostic environment 100 of FIG. 1, including select components of at least one compartment of ophthalmic device 150, arranged coaxially, according to an embodiment of the invention. Identically referenced elements of the at least one compartment are similar to those described in connection with FIG. 2, except that the embodiment depicted in FIG. 3 also includes a mirror 156. In this configuration, mirror 156 is positioned inline relative to image sensor 162, lens 160, and the opening at patient-facing side of the apparatus. Light source 152 is positioned below mirror 156 along a second axis, i.e., the y-axis. This configuration is referred to as coaxial. In an embodiment, mirror 156 is a 25 mm (5×5 mm) front surface mirror, positioned at a 45-degree angle relative to light source 152. When light source 152 is energized, it emits light beams that hit the mirror and bounce towards the opening of the apparatus at the patient-facing side. The light beams hit and bounce off of the patient's eye(s) 112.

FIG. 4 is a partial diagram of a dual-compartment configuration of the medical diagnostic environment 100 of FIGS. 1 and 2, including select components of ophthalmic device 150, arranged inline, according to an embodiment of the invention. The components depicted and referenced in FIGS. 1 and 2 are arranged in two adjacent compartments each having an opening along the patient-facing side of ophthalmic device 150. The two adjacent compartments may also be referred to as a first compartment and as a second compartment.

The dual-compartment configuration depicted in FIG. 4 enables inducement of simultaneous pupil dilation in both eyes of the patient, i.e. user 110, and further enables asynchronous and disparate emission of light beams towards the patient's eyes. For example, visible light beams from light source 152 can be directed at a first eye without also directing visible light beams at a second eye.

The ophthalmic device 150 shown in FIG. 4 may be operated and controlled according in the manner described in connection with FIG. 8 to perform one or more methods, according to embodiments of the invention. More specifically, the control unit (or other components) of ophthalmic device 150 may include a processor and a tangible storage device storing program instructions executable by the processor.

FIG. 5 is a partial diagram of a dual-compartment configuration of the medical diagnostic environment 100 of FIGS. 1 and 2, including select components of ophthalmic device 150, arranged coaxially, according to an embodiment of the invention. The coaxial configuration is one alternative to the inline configuration shown in FIG. 4. The components depicted and referenced in FIGS. 1 and 2 are arranged in two adjacent compartments each having an opening along the patient-facing side of ophthalmic device 150. The two adjacent compartments may also be referred to as a first compartment and as a second compartment.

The dual-compartment configuration depicted in FIG. 5 enables inducement of simultaneous pupil dilation in both eyes of the patient, i.e. user 110, and further enables asynchronous and disparate emission of light beams towards the patient's eyes. For example, visible light beams from light source 152 can be directed at a first eye without also directing visible light beams at a second eye.

The ophthalmic device 150 shown in FIG. 5 may be operated and controlled according in the manner described in connection with FIG. 8 to perform one or more methods, according to embodiments of the invention. More specifically, the control unit (or other components) of ophthalmic device 150 may include a processor and a tangible storage device storing program instructions executable by the processor.

Referring now generally to FIGS. 4 and 5, ophthalmic device 150 may include a pair of light emitting devices (light sources 152) configured to emit a light beam onto a pair of target eyes (of user 110). The light beam can be infrared light or visible light. Ophthalmic device includes one opening or a pair of openings 180 (FIG. 1) configured to couple with the pair of target eyes to block light external to the apparatus from hitting the pair of target eyes. A pair of image sensors 162 are configured to capture light reflected from the pair of target eyes. A pair of lenses 160 are configured to focus light reflected from the pair of target eyes onto the pair of image sensors 162. A controller unit is configured to illuminate the pair of target eyes with a plurality of successively more energetic light beams within a period of time.

Reference will now be made to exemplary methods, in FIGS. 6A-C and 7A-D, for operating various components of ophthalmic device 150 (ophthalmic device 150 and its components are described in connection with FIGS. 1-5). These methods include those for operating a single compartment configuration, and a dual compartment configuration.

FIG. 6A is a flowchart of a method 600 for using an ophthalmic device, according to an embodiment of the invention. For example, the method may be performed by ophthalmic device 150 depicted in FIGS. 2-3, by executing programming instructions of the method via the processor of the control unit of ophthalmic device 150. Method 600 may be performed to operate a first compartment (FIGS. 2 and 3) of the two compartments of ophthalmic device 150 (as shown in FIGS. 1, 4 and 5), without necessarily operating a second compartment at the same time or in the same manner. Although steps of method 600 are listed in a particular order, they may be performed in any other order suitable for the particular desired use case. Therefore, the recited order shall not be construed as limiting the scope of the invention to that recited order.

Now with reference to FIGS. 1-3 and 6A, in accordance with an embodiment of the invention, method 600 may be performed, by a processor of ophthalmic device 150 executing program instructions stored on a tangible storage device of ophthalmic device 150. Executing various programming instructions enables operation of the various components of ophthalmic device 150.

Prior to execution of method 600, opening 180 of ophthalmic device 150 is placed in contact with user 110, i.e. a patient, such that the opening completely or substantially covers at least the patient's eye(s) and/or eye socket(s). This process triggers the patient's natural response to low light conditions, whereby the patient's pupils begin dilating naturally. Full natural dilation typically occurs within a few minutes, which is much faster than chemically induced pupil dilation.

Method 600 may be initiated manually (e.g., by pressing a button) or automatically (by detecting low level lighting conditions at opening 180, or by other sensor technology that detects the patient coming into contact with opening 180). For example, image sensor 162 can monitor the amount of light reflected within ophthalmic device 150. Ophthalmic device 150 can initiate method 600 when lighting conditions as captured by image sensor 162 match an initiation criteria.

At a point in time after initiation, the processor of ophthalmic device 150 causes the power source to energize the infrared light source (in one embodiment, this is a component of a single light source unit, or a separate light source) of light source 152. Upon being energized, the infrared light source emits (step 604) infrared light in the direction of opening 180 (targeting the patient's eyes) for a period of time (in one embodiment, the period of time is 30 seconds). The beams of infrared light, emitted during the period of time, travel towards the patient's eye and illuminate (via infrared light) the eye and the fundus. The beams of infrared light are then reflected back into ophthalmic device 150.

Image sensor 162 captures (step 608) the reflected infrared light. In an embodiment, mirror 160 collimates the reflected beams of infrared light before image sensor 162 receives them, for better image quality. Image sensor 162 stores the reflected infrared light into a series of images and/or video.

Image sensor 162 identifies (step 612) an image of an eye, in captured reflection of infrared light, by analyzing the captured reflection of the infrared light using pixel information. Image sensor 162 uses image recognition algorithms to identify, in the captured image (or video), the shape of an eye and/or its various anatomical structures, including pupils and their size. In an embodiment, the pupil dilation measurement algorithm may be as set forth in Table 1: Illustrative Programming Code for Processing Image/Video Data Captured by Image Sensor 162, below.

TABLE 1

Illustrative Programming Code
for Processing Image/Video Data Captured by Image Sensor 162

```
import numpy as np
import cv2
vid='filepath/filename.avi'
MAX_GRAY=50; # detection sensitivity, smaller=more sensitive
square=30; # 1/3 size of side of square startY=120; step=16;
frameCount=0; # frame counter
clip = lambda x, l, u: l if x < l else u if x > u else x # clip routine
clip(var,min,max)
def matchFilter(im):
    hitCount=0
    for y in range(startY,yRez-3*square,step):
```

TABLE 1-continued

Illustrative Programming Code
for Processing Image/Video Data Captured by Image Sensor 162

```
        for x in range(0,xRez-3*square,step):
            x0=x; x1=x0+square; x2=x1+square; x3=x2+square;
            y0=y; y1=y0+square; y2=y1+square; y3=y2+square;
            a=0; b=0;
            a=np.sum(im[y0:y1,x0:x3])# top bar;
            a+=np.sum(im[y2:y3,x0:x3]) # bottom bar;
    a+=np.sum(im[y1:y2,x0:x1])# left square; a+=np.sum(im[y1:y2,x2:x3])#
right square;
    b=np.sum(im[y1:y2,x1:x2])# inner square
            r=128+(a-8*b)/(square*square)
            if r>200:
                result[y,x]=255
                hitCount+=1
            else:
                result[y,x]=0
    return(hitCount)
cap = cv2.VideoCapture(vid)
START=0; STOP=1000;
frameCount=0;
cap.set(cv2.CAP_PROP_POS_FRAMES, START)
result=np.zeros((yRez,xRez))
while(cap.isOpened( )):
    ret, frame = cap.read( )
    if not ret:
        break
    gray = cv2.cvtColor(frame, cv2.COLOR_BGR2GRAY)
    hitCount=matchFilter(gray)
    print frameCount,hitCount
    frameCount+=1 # frame counter
cap.release( )
```

Image sensor 162 measures (step 616) pupil dilation in the eye by analyzing the identified image of the eye. Measuring pupil dilation includes measuring, at any given point in time, pupil diameter in the eye; and measuring pupil diameter at another time. The two measured pupil diameters are compared to one another. If the pupil diameter in the first measurement is smaller than the pupil diameter in the second measurement, the pupil has dilated. If the pupil diameter in the second measurement is smaller than the pupil diameter in the first measurement, the pupil has contracted.

The processor of ophthalmic device 150 determines (step 620) that pupil dilation (assuming it occurs) is dilated by a first amount greater than or equal to a pre-configured dilation measurement. This may be performed using a loop by which the patient's eye is illuminated for the period of time (e.g., 30 seconds), and the processor monitors the output of image sensor 162 to determine the amount of pupil dilation. During the monitoring, the processor checks whether pupil dilation has reached a desired level (e.g., full dilation or another amount of dilation).

The preconfigured dilation measurement may be an absolute value or a relative value, and it may be set to a value most appropriate for the given patient. For example, a fully dilated pupil may vary in size from one patient (or patient group) to another. The same is true as between pupils in humans as compared to animals. Therefore, a single universal value for full pupil dilation might not be ideal. By allowing a user to define a preconfigured dilation measurement, ophthalmic device 150 can illuminate the eye continuously until a desired level of pupil dilation is detected in the particular patient.

Light source 152, via its visible light source, may emit (step 624) at least two beams of visible light in sequence, during a period of time for visible light emission, by energizing the visible light source via the power source. The at least two beams of visible light include a first beam of visible light having a first energy and a second beam of visible light having a second energy greater than the first energy. For example, a red LED may be energized first, because red light has a relatively long wavelength, a relatively low frequency, and a relatively low photon energy. Then one or more additional LEDs having a different color, such as orange, yellow, green, etc., would be energized sequentially, according to a descending order of wavelength, and ascending order of frequency and photon energy.

The described visible light emission process (step 624) takes advantage of the pupillary reflex, whereby the pupil constricts in response to visible light radiation. Visible light beams radiate onto the target eye and cause a pupillary constriction reflex.

According to an embodiment of the invention, the period of time for visible light emission (step 624) is greater than zero and less than or equal to 200 milliseconds.

According to an embodiment of the invention, each of the at least two beams of visible light are emitted (step 624) for an equal portion of the period of time for visible light emission.

FIG. 6B is a flowchart of additional steps of method 600 (FIG. 6A) for using an ophthalmic device, according to an embodiment of the invention.

Now with reference to FIGS. 1-3 and 6A and 6B, in accordance with an embodiment of the invention, image sensor 162 detects (step 628) a response time of pupil constriction in the eye in response to emitting the at least two beams of visible light. Detecting the response time of pupil constriction may be performed by capturing images (or video) of the eye (reflections of visible light radiation) by image sensor 162 and analyzing the images to detect changes in the size of the pupil. In an embodiment, the detection may be performed using the algorithm provided in Table 1: Illustrative Programming Code for Processing Image/Video Data Captured by Image Sensor 162, above.

Based on the detection (step 628) of the of response time of pupil constriction, the processor generates (step 632) a delta report comprising data showing a divergence between the measured response time of pupil constriction and an expected response time of pupil constriction. The expected respect time of pupil constriction may be a preconfigured value. The preconfigured value may be, for example, a statistically measured response time in a sample population of healthy patients. The delta report may display, for example, the expected response time of pupil constriction, the measured response time of pupil constriction, and a measure of divergence between the two. A higher than normal divergence may be particularly highlighted to denote a possible ailment.

The I/O device of ophthalmic device 150 may output (636) the delta report. The output generally may include any known outputting method (including visual and auditory), and particularly may include displaying the delta report onto a screen and communicating the delta report to a device (such as a mobile phone or a cloud service).

FIG. 6C is a flowchart of additional steps of method 600 (FIGS. 6A and 6B) for using an ophthalmic device, according to an embodiment of the invention.

Now with reference to FIGS. 1-3, 6A, 6B, and 6C, in accordance with an embodiment of the invention, the infrared light source emits (640) a beam of infrared light (in an embodiment, this may be at least two beams of infrared light each having a different energy).

Image sensor 162 captures (644) a reflection of each of the at least two beams of infrared light, and the I/O device outputs (648) one or more images of the captured reflection of each of the at least two beams of infrared light.

With general reference to FIGS. 6A, 6B, 6C, it shall be understood by a person of ordinary skill in the art that performing the described steps by executing corresponding programming instructions enables ophthalmic device 150 (FIG. 1) to capture, in a single compartment configuration, internal images of the fundus using infrared light, and to capture images of the pupillary reflex using visible light (as determined by a divergence between an expected pupillary constriction response and a measured pupillary constriction response). Ophthalmic device 150 may perform these steps at the same time period, at overlapping time periods, or at different time periods. This versatility does not exist in the prior art.

FIG. 7A is a flowchart of a method 700 for using an ophthalmic device, according to an embodiment of the invention. For example, the method may be performed by ophthalmic device 150 depicted in FIGS. 4-5, by executing programming instructions of the method via the processor of the control unit of ophthalmic device 150. Method 700 may be performed to operate a dual compartment configuration of ophthalmic device 150 (as shown in FIGS. 1, 4 and 5). Although steps of method 700 are listed in a particular order, they may be performed in any other order suitable for the particular desired use case. Therefore, the recited order shall not be construed as limiting the scope of the invention to that recited order.

Now with reference to FIGS. 1, 4-5, and 7A, in accordance with an embodiment of the invention, method 700 may be performed, by a processor of ophthalmic device 150 executing program instructions stored on a tangible storage device of ophthalmic device 150. Executing various programming instructions enables operation of the various components of ophthalmic device 150 in either the first compartment, the second compartment, or both. Each compartment may be controlled in the same way as or in a different way than the other compartment.

Prior to execution of method 700, opening 180 of ophthalmic device 150 is placed in contact with user 110, i.e. a patient, such that the opening completely or substantially covers at least the patient's eye(s) and/or eye socket(s). This process triggers the patient's natural response to low light conditions, whereby the patient's pupils begin dilating naturally. Full natural dilation typically occurs within a few minutes, which is much faster than chemically induced pupil dilation.

Respective infrared light sources (of light sources 152) of the first compartment and the second compartment emit (step 704) infrared light in the direction of the opening for a period of time by energizing the infrared light source via the power source. Alternatively, the infrared light source of only one compartment is energized.

Respective image sensors 162 of the first compartment and the second compartment capture (step 708) a reflection of the infrared light. Alternatively, where only the infrared light source of one compartment is energized, only the corresponding image sensor 162 captures the reflection.

Respective image sensors 162 of the first compartment and the second compartment identify (step 712) an image of an eye (i.e., the respective eye targeted at each compartment) by analyzing the captured reflection of the infrared light.

Respective image sensors 162 of the first compartment and the second compartment measure (step 716) pupil dilation in the eye (i.e., the respective eye targeted at each compartment) by analyzing the identified image of the eye.

The processor (or multiple processors) determine (step 720), for each of the first compartment and the second compartment (assuming both compartments are engaged), that the pupil (of the respective eye targeted) is dilated by a first amount greater than or equal to a pre-configured dilation measurement.

Either or both of respective visible light sources of the first compartment and the second compartment emit (step 724) at least two beams of visible light in sequence in one compartment, during a period of time for visible light emission, by energizing the visible light source via the power source. The at least two beams of light include a first beam of visible light having a first energy and a second beam of visible light having a second energy greater than the first energy. Selective emission of light in one compartment but not the other allows for testing of the pupillary reflex, by determining whether the non-illuminated eye constricts in the same way and amount as the illuminated eye, as would be expected in a healthy patient. Were both eyes to be illuminated at the same time and in the same way, it might not be possible to detect whether the patient is experiencing a lack of synchronicity in the pupillary reflex.

According to an embodiment, the period of time for visible light emission (step 724) is greater than zero and less than or equal to 200 milliseconds. In an embodiment, each of the at least two beams of visible light are emitted (step 724) for an equal portion of the period of time for visible light emission.

FIG. 7B is a flowchart of additional steps of method 700 (FIG. 7A) for using an ophthalmic device, according to an embodiment of the invention.

Now with reference to FIGS. 1, 4-5 and 7A and 7B, in accordance with an embodiment of the invention, image sensor 162 (of the first compartment, the second compartment, or both) detects (step 728) a response time of pupil constriction in the eye in response to emitting the at least two beams of visible light in the first compartment, the second compartment, or both.

The processor generates (step 732) a delta report that includes data showing a divergence between the measured response time of pupil constriction and an expected response time of pupil constriction.

The I/O device outputs (step 736) the delta report.

FIG. 7C is a flowchart of additional steps of method 700 (FIG. 7A) for using an ophthalmic device, according to an embodiment of the invention.

Now with reference to FIGS. 1, 4-5 and 7A, 7B, and 7C, in accordance with an embodiment of the invention, image sensor 162 of the first compartment detects (step 740) a response time of pupil constriction in the eye positioned at the opening of the first compartment, in response to emitting the at least two beams of visible light in the first compartment. Emission (at step 740) of the at least two beams of visible light in sequence is exclusive to the first compartment (or exclusive to the second compartment) for the period of time for visible light emission.

The processor generates (step 744) a delta report including data showing a divergence between the measured response time of pupil constriction of the eye in the first compartment and the measured response time of pupil constriction of the eye in the second compartment.

The I/O device outputs (step 748) the delta report.

FIG. 7D is a flowchart of additional steps of method 700 (FIG. 7A) for using an ophthalmic device, according to an embodiment of the invention.

Now with reference to FIGS. 1, 4-5 and 7A, 7B, 7C and 7D, in accordance with an embodiment of the invention, respective infrared light sources 152 of the first compartment and the second compartment emit (step 752) a beam of infrared light (in an embodiment, this may be at least two beams of infrared light each having a different frequency). Alternatively, infrared light source 152 of only one compartment emits at least two beams of infrared light. Alternatively, whether one or two compartments are used, only one beam of infrared light is emitted.

Respective image sensors 162 of the first compartment and the second compartment capture (step 756) a reflection of each of the at least two beams of infrared light.

The I/O device outputs (step 760) one or more images of the captured reflection of each of the at least two beams of infrared light in the first compartment and the second compartment.

With general reference to FIGS. 7A, 7B, 7C, and 7D, it shall be understood by a person of ordinary skill in the art that performing the described steps by executing corresponding programming instructions enables ophthalmic device 150 (FIG. 1) to capture, in a dual compartment configuration, internal images of the fundus using infrared light, and to capture images of the pupillary reflex using visible light (as determined by a divergence between an expected pupillary constriction response and a measured pupillary constriction response). Ophthalmic device 150 may perform these steps at the same time period, at overlapping time periods, or at different time periods. This versatility does not exist in the prior art.

Now with reference to FIGS. 1-5, in accordance with an embodiment of the invention, a method may be performed, by a processor of ophthalmic device 150 executing program instructions stored on a tangible storage device of ophthalmic device 150. Executing various programming instructions enables operation of the various components of ophthalmic device 150 in either the first compartment, the second compartment, or both. Each compartment may be controlled in the same way as or in a different way than the other compartment.

The pair of target eyes are covered with one or a pair of external-light blocking eyepieces of ophthalmic device 150. The covering includes positioning the pair of external-light blocking eyepieces in contact with the patient's face.

Ophthalmic device 150 monitors pupil dilation of the target pairs of eyes for a period of time while the pair of external-light blocking eyepieces are in contact with the patient's face. In an embodiment, the monitoring includes detecting pupils of the target pairs of eyes reaching maximum dilation. Executing other steps of the method may be conditioned, in some embodiments, on detecting that pupil dilation has reached maximum dilation.

A pair of light sources 152 of ophthalmic device 150 emit, based on the monitoring, infrared light at the pair of target eyes.

A pair of image sensors 162 of the ophthalmic device 150 detect infrared light reflected by the pair of target eyes in response to the emission of infrared light by the pair of light sources 152.

In an embodiment, one of the light sources 152 selectively emit towards a first eye in the pair of target eyes, at least two beams of visible light in sequence, during a period of time for visible light emission, by energizing the light source via a power source. The at least two beams of light include a first beam of visible light having a first energy and a second beam of visible light having a second energy greater than the first energy.

In an embodiment, the method further includes capturing images of the first eye and the second eye, and measuring, based on the captured images, a response time of pupil constriction in the first eye relative to pupil constriction in a second eye in the pair of target eyes. The method generates a delta report comprising data showing a divergence between the measured response times of pupil constriction in the first eye and the second eye. The method outputs, by an I/O device of the apparatus, the delta report.

In an embodiment, the period of time for visible light emission is greater than zero and less than or equal to 200 milliseconds.

In an embodiment, the emitting further includes emitting, selectively by one of the light sources towards a first eye in the pair of target eyes, at least one beam for each distinct visible light spectrum color, in sequence from least energized to most energized.

In an embodiment, the pupil dilation during at least a portion of the period of time for visible light emission is less than 100%.

Referring now generally to embodiments of the invention, aspects of the invention may include processes that are performed, in part, on a cloud computing network. For example, aspects of the invention may be provided as or via a cloud computing service.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 9, an illustrative cloud computing environment 50 is depicted. As shown, cloud computing environment 50 includes one or more cloud computing nodes 10 (each of which may be as described in connection with FIG. 8) with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Referring now to FIG. 10, a set of functional abstraction layers provided by cloud computing environment 50 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and retinal and fundus image processing 96 (as described in connection with FIGS. 1-8).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for examining a pair of target eyes of a patient using an apparatus, the method comprising:
    covering the pair of target eyes with one or a pair of external-light blocking eyepieces of the apparatus, the covering comprising positioning the pair of external-light blocking eyepieces in contact with the patient's face;
    monitoring pupil dilation of the target pairs of eyes for a period of time while the pair of external-light blocking eyepieces are in contact with the patient's face; and
    emitting, by a pair of light sources of the apparatus based on the monitoring, infrared light at the pair of target eyes;
    detecting, using a pair of image sensors of the apparatus, infrared light reflected by the pair of target eyes in response to the emission of infrared light by the pair of light sources capturing images of the first eye and the second eye;
    measuring, based on the captured images, a response time of pupil constriction in the first eye relative to pupil constriction in a second eye in the pair of target eyes;
    generating a delta report comprising data showing a divergence between the measured response times of pupil constriction in the first eye and the second eye; and
    outputting, by an I/O device of the apparatus, the delta report.

2. The method of claim 1, wherein the monitoring comprises:
    detecting pupils of the target pairs of eyes reaching maximum dilation.

3. The method of claim 1, further comprising:
    emitting, selectively by one of the light sources towards a first eye in the pair of target eyes, at least two beams of visible light in sequence, during a period of time for visible light emission, by energizing the light source via a power source, the at least two beams of light comprising a first beam of visible light having a first energy and a second beam of visible light having a second energy greater than the first energy.

4. The method of claim 3, wherein the period of time for visible light emission is greater than zero and less than or equal to 200 milliseconds.

5. The method of claim 3, wherein the emitting further comprises:
    emitting, selectively by one of the light sources towards a first eye in the pair of target eyes, at least one beam for each distinct visible light spectrum color, in sequence from least energized to most energized.

6. The method of claim 3, wherein pupil dilation during at least a portion of the period of time for visible light emission is less than 100%.

* * * * *